(12) United States Patent
Miyagi et al.

(10) Patent No.: US 8,921,515 B2
(45) Date of Patent: Dec. 30, 2014

(54) METHODS AND COMPOSITIONS OF PREPARATION FOR PROTEOME ANALYSIS

(71) Applicant: Case Western Reserve University, Cleveland, OH (US)

(72) Inventors: Masaru Miyagi, Shakar Heights, OH (US); Chandra Sekhar Rao Kadiyala, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/727,646

(22) Filed: Dec. 27, 2012

(65) Prior Publication Data

US 2013/0172539 A1 Jul. 4, 2013

Related U.S. Application Data

(60) Provisional application No. 61/580,797, filed on Dec. 28, 2011.

(51) Int. Cl.
*C07K 1/14* (2006.01)
*C07K 1/30* (2006.01)
*A61K 38/00* (2006.01)
*C07K 1/00* (2006.01)
*C07K 1/02* (2006.01)

(52) U.S. Cl.
CPC . *C07K 1/145* (2013.01); *C07K 1/00* (2013.01); *C07K 1/30* (2013.01); *C07K 1/02* (2013.01); *C07K 1/14* (2013.01)
USPC ........ 530/300; 435/86; 424/184.1; 424/185.1

(58) Field of Classification Search
USPC .................. 424/184.1, 185.1; 435/23, 86
See application file for complete search history.

*Primary Examiner* — Rodney P Swartz
(74) *Attorney, Agent, or Firm* — Tarolli, Sundheim, Covell & Tummino LLP

(57) ABSTRACT

A method of extracting a polypeptide from a biological sample includes contacting the biological sample with an extraction reagent to form a solution of the biological sample and the extraction reagent. The extraction reagent includes perfluorooctanoic and can be used at a concentration effective to solubilize the polypeptides in the biological sample.

22 Claims, 5 Drawing Sheets

```
                       SEQUENCE LISTING

<160> NUMBER OF SEQ ID NOS: 21

<210> SEQ ID NO 1
<211> LENGTH: 7
<212> TYPE: PRT
<213> ORGANISM: Homo sapiens

<400> SEQUENCE: 1

Leu Val Thr Asp Leu Thr Lys
1               5

<210> SEQ ID NO 2
<211> LENGTH: 7
<212> TYPE: PRT
<213> ORGANISM: Homo sapiens

<400> SEQUENCE: 2

Tyr Ile Tyr Glu Ile Ala Arg
1               5

<210> SEQ ID NO 3
<211> LENGTH: 14
<212> TYPE: PRT
<213> ORGANISM: Homo sapiens

<400> SEQUENCE: 3

Val Pro Gln Val Ser Thr Pro Thr Leu Val Glu Val Ser Arg
1               5                   10

<210> SEQ ID NO 4
<211> LENGTH: 10
<212> TYPE: PRT
<213> ORGANISM: Homo sapiens

<400> SEQUENCE: 4

Leu Val Asn Glu Leu Thr Glu Phe Ala Lys
1               5                   10

<210> SEQ ID NO 5
<211> LENGTH: 15
<212> TYPE: PRT
<213> ORGANISM: Homo sapiens

<400> SEQUENCE: 5

Lys Val Pro Gln Val Ser Thr Pro Thr Leu Val Glu Val Ser Arg
1               5                   10                  15

<210> SEQ ID NO 6
<211> LENGTH: 10
<212> TYPE: PRT
<213> ORGANISM: Homo sapiens
```

```
<400> SEQUENCE: 6

Lys Gln Thr Ala Leu Val Glu Leu Leu Lys
1               5                   10

<210> SEQ ID NO 7
<211> LENGTH: 8
<212> TYPE: PRT
<213> ORGANISM: Homo sapiens

<400> SEQUENCE: 7

Ala Glu Phe Val Glu Val Thr Lys
1               5

<210> SEQ ID NO 8
<211> LENGTH: 16
<212> TYPE: PRT
<213> ORGANISM: Homo sapiens

<400> SEQUENCE: 8

Arg His Pro Tyr Phe Tyr Ala Pro Glu Leu Leu Tyr Tyr Ala Asn Lys
1               5                   10                  15

<210> SEQ ID NO 9
<211> LENGTH: 12
<212> TYPE: PRT
<213> ORGANISM: Homo sapiens

<400> SEQUENCE: 9

Arg His Pro Glu Tyr Ala Val Ser Val Leu Leu Arg
1               5                   10

<210> SEQ ID NO 10
<211> LENGTH: 13
<212> TYPE: PRT
<213> ORGANISM: Homo sapiens

<400> SEQUENCE: 10

Leu Gly Glu Tyr Gly Phe Gln Asn Ala Leu Ile Val Arg
1               5                   10

<210> SEQ ID NO 11
<211> LENGTH: 12
<212> TYPE: PRT
<213> ORGANISM: Homo sapiens

<400> SEQUENCE: 11

Ser Leu His Thr Leu Phe Gly Asp Glu Leu Cys Lys
1               5                   10

<210> SEQ ID NO 12
<211> LENGTH: 13
<212> TYPE: PRT
<213> ORGANISM: Homo sapiens

<400> SEQUENCE: 12

Leu Lys Pro Asp Pro Asn Thr Leu Cys Asp Glu Phe Lys
1               5                   10

<210> SEQ ID NO 13
<211> LENGTH: 13
<212> TYPE: PRT
<213> ORGANISM: Homo sapiens
```

```
<400> SEQUENCE: 13

Asp Ala Phe Leu Gly Ser Phe Leu Tyr Glu Tyr Ser Arg
1               5                   10

<210> SEQ ID NO 14
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Oxidation

<400> SEQUENCE: 14

Met Pro Cys Thr Glu Asp Tyr Leu Ser Leu Ile Leu Asn Arg
1               5                   10

<210> SEQ ID NO 15
<211> LENGTH: 14
<212> TYPE: PRT
<213> ORGANISM: Homo sapiens

<400> SEQUENCE: 15

Tyr Asn Gly Val Phe Gln Glu Cys Cys Gln Ala Glu Asp Lys
1               5                   10

<210> SEQ ID NO 16
<211> LENGTH: 12
<212> TYPE: PRT
<213> ORGANISM: Homo sapiens

<400> SEQUENCE: 16

Thr Val Met Glu Asn Phe Val Ala Phe Val Asp Lys
1               5                   10

<210> SEQ ID NO 17
<211> LENGTH: 14
<212> TYPE: PRT
<213> ORGANISM: Homo sapiens

<400> SEQUENCE: 17

Glu Cys Cys His Gly Asp Leu Leu Glu Cys Ala Asp Asp Arg
1               5                   10

<210> SEQ ID NO 18
<211> LENGTH: 12
<212> TYPE: PRT
<213> ORGANISM: Homo sapiens

<400> SEQUENCE: 18

Glu Tyr Glu Ala Thr Leu Glu Glu Cys Cys Ala Lys
1               5                   10

<210> SEQ ID NO 19
<211> LENGTH: 13
<212> TYPE: PRT
<213> ORGANISM: Homo sapiens

<400> SEQUENCE: 19

Thr Cys Val Ala Asp Glu Ser His Ala Gly Cys Glu Lys
1               5                   10
```

```
<210> SEQ ID NO 20
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Oxidation

<400> SEQUENCE: 20

Glu Thr Tyr Gly Asp Met Ala Asp Cys Cys Glu Lys
1               5                   10

<210> SEQ ID NO 21
<211> LENGTH: 12
<212> TYPE: PRT
<213> ORGANISM: Homo sapiens

<400> SEQUENCE: 21

Glu Thr Tyr Gly Asp Met Ala Asp Cys Cys Glu Lys
1               5                   10
```

METHODS AND COMPOSITIONS OF PREPARATION FOR PROTEOME ANALYSIS

RELATED APPLICATION

This application claims priority from U.S. Provisional Application No. 61/580,797, filed Dec. 28, 2011, the subject matter, which is incorporated herein by reference in its entirety.

BACKGROUND

Shotgun proteomics experiments use surfactants to achieve efficient extraction and digestion of proteins. The surfactants widely used in shotgun proteomics can be classified as ionic (e.g., sodium dodecyl sulfate (SDS)), nonionic (e.g., Triton-X), and acid cleavable surfactants (e.g., RapiGest). A typical strategy for shotgun proteomics of samples containing membrane proteins begins with protein extraction from cells or tissues in the presence of a surfactant, then cystine residues are reduced and alkylated under denaturing conditions, and then the surfactant is subsequently removed by acetone precipitation or by exchange with urea on a standard filtration device. The resulting acetone precipitate is generally solubilized either in a strong chaotropic agent, such as urea or guanidine hydrochloride (Gdn-HCl) or in a surfactant, and then subjected to proteolytic digestion. After the digestion, the chaotropic agent are removed by a reverse-phase solid phase extraction. However, when a surfactant is used, it cannot be removed easily from the digest. Because surfactants are hydrophobic in nature, they cause peak broadening and suppress the ionization of peptides in the subsequent LC-MS/MS analysis. Thus, the surfactants used must be removed prior to LC-MS/MS analysis.

Surfactants can be removed from peptide mixtures either by ion exchange chromatography, by phase transfer, or by washing with chlorinated solvents while peptides are captured on a reversed phase cartridge. These extra preparation steps have the major drawback of losing peptides to the stationary phase during the procedures, which cannot be afforded when sample amount is limited. To avoid this problem, acid labile surfactants have been developed that can be cleaved between the hydrophobic and hydrophilic part of the surfactants after the protein digestion. The hydrophobic part precipitates upon the acid cleavage, allowing its removal from the digest. The hydrophilic part does not interfere with the subsequent LC-MS/MS analysis. However, it has been reported that hydrophobic peptides are lost from the digest due to their interactions with the precipitated hydrophobic part of the surfactant. Thus, a method is needed that does not lead to the loss of peptides.

SUMMARY

Embodiments described herein relate to kits for and methods of extracting a polypeptide or protein from a biological sample. In some embodiments, the method can include contacting the biological sample with an extraction reagent to form a solution of the biological sample and the extraction reagent. The extraction reagent can include perfluorooctanoic acid and be used to solubilize the polypeptides or proteins in the biological sample. Solubilization of the polypeptides or proteins with perfluorooctanoic acid in the methods described herein is comparable to sodium dodecyl sulfate (SDS) and, unlike SDS, is compatible with proteolytic digestion, e.g., trypsin digestion. The perfluorooctanoic acid can be readily removed following extraction of the polypeptides or proteins, which allows the method to be used in shotgun proteomics and subsequent mass spectrometry analysis.

In some embodiments, the perfluorooctanoic acid can be provided in the extraction reagent at concentration of up to 2% w/v of the extraction reagent. The extraction reagent can further include at least one of a reducing agent and an s-alkylating agent to promote denaturing of the solubilized polypeptides or proteins.

In other embodiments, the method can further include contacting the solution with a proteolytic enzyme to digest the polypeptides or proteins in the solution. The concentration of perfluorooctanoic acid in the solution is such that it does not substantially inhibit proteolytic digestion. For example, the concentration of perfluorooctanoic acid in the solution during proteolytic digestion can be about 0.1% w/v to about 0.5% w/v.

In some embodiments, the perfluoroctanoic acid can be removed from the solution following polypeptide or protein digestion by evaporation, chromatography, or solid phase extraction. For example, the perfluorooctanoic acide can be removed from the polypeptide or protein digest using at least one of strong cation exchange chromatography, hydrophilic interaction chromatography, fluorous solid phase extraction, or anion exchange chromatography.

Figure 1:
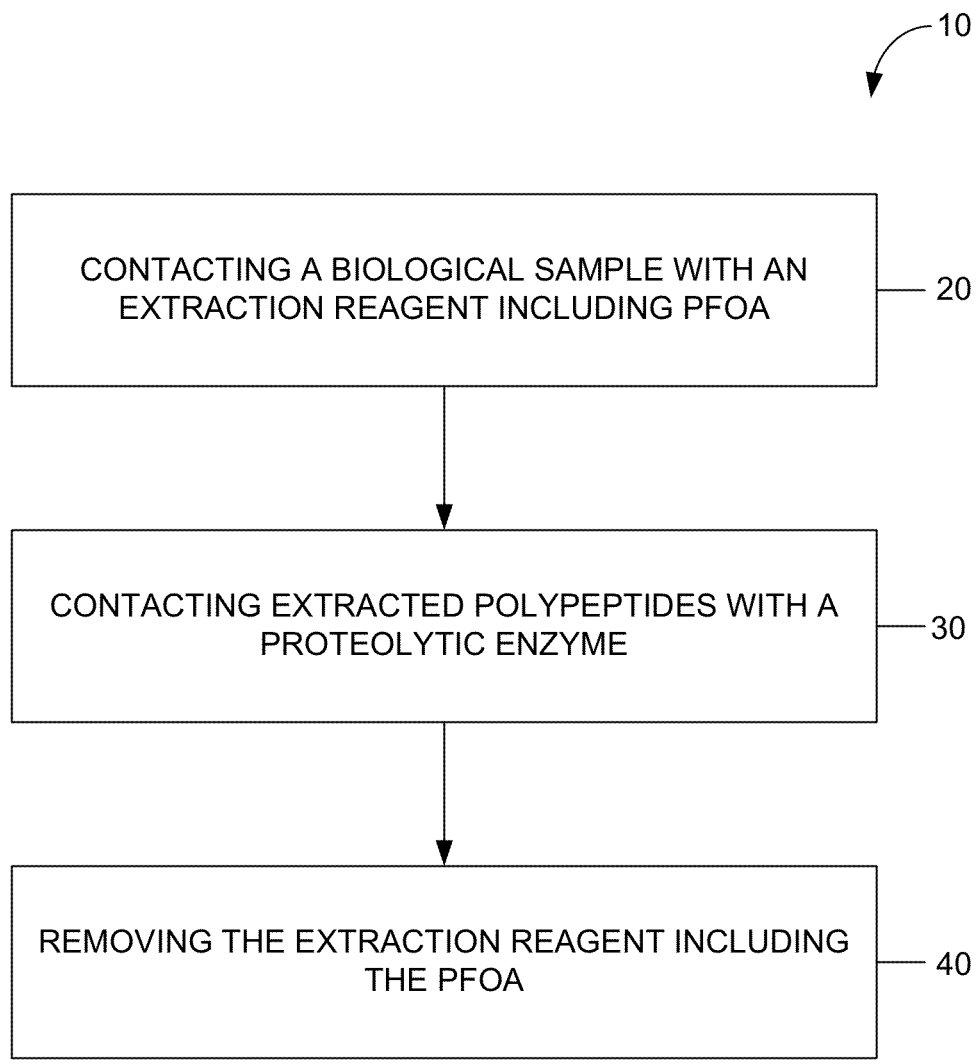
FIG. 1 is a flow diagram illustrating an extraction method in accordance with an embodiment described herein.

ACN at 50 μL/min) The (M-H)⁻ ion (m/z 413) of PFOA was monitored. The PFOA amounts in the parentheses are calculated based on the dilution factors for the samples. Peaks a (211.1 μg), b (below detection limit), c (below detection limit), and d (trace amount) represent the estimated PFOA amount in the flow through, washing 1, washing 2, and high-salt elution fractions from SCX chromatography, respectively. Peaks e (181.7 μg), f (trace amount), g (below detection limit), and h (below detection limit) represent the flow through, washing 1, washing 2, and low-organic elution fractions from HILIC chromatography, respectively. Peaks i (trace amount), j (81.8 μg), k (22.9 μg), and l (2.3 μg) represent the flow through, 70%, 80%, and 100% methanol washing fractions from FSPE chromatography, respectively. Peaks m (141.2 μg), n (below detection limit), and o (below detection limit) represent the flow through, washing 1, and washing two fractions from ANX chromatography, respectively.

DETAILED DESCRIPTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The "sample" or "biological sample" or "composition" to be purified herein comprises the polypeptide or protein of interest and one or more impurities. The sample may be "partially purified" (i.e., having been subjected to one or more purification steps, such as by chromatography described herein or may be obtained directly from a host cell or organism producing the polypeptide (e.g., the sample may comprise harvested cell culture fluid).

The term, "polypeptide" refers generally to peptides and proteins having more than about ten amino acids. Preferably, the polypeptide is a mammalian protein, examples of which include transmembrane proteins. In addition, a protein or polypeptide can be an antibody, fragment or variant thereof.

The term "impurity" refers to a material that is different from the desired polypeptide product or protein of interest. The impurity includes, but is not limited to, a host cell protein (HCP), a polypeptide other than the target polypeptide, nucleic acid, endotoxin etc.

The term "acidic variant" or a variant of a polypeptide of interest which is more acidic (e.g., as determined by cation exchange chromatography) than the polypeptide of interest. An example of an acidic variant is a deamidated variant.

The terms "protein of interest" and "target protein" are used interchangeably and refer to a protein or polypeptide, such as an antibody that is to be purified by a method of the invention from a mixture of proteins and, optionally, other materials such as cell debris and the like.

The term "parts per million" or "ppm" are used interchangeably and refer to a measure of purity of the protein of interest purified by a method described herein.

By "purifying" a polypeptide from a composition comprising the polypeptide and one or more impurities is meant increasing the degree of purity of the polypeptide in the composition by removing (completely or partially) at least one impurity from the composition. Purification can be performed without the use of a chromatography step. A "purification step" may be part of an overall purification process resulting in a "homogeneous" composition, which is used herein to refer to a composition comprising less than 100 ppm protein in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g., antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g., antibody) and a solid phase matrix.

The term, "solvent" refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The terms "ion-exchange" and "ion-exchange chromatography" refer to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode chromatography.

The phrase "ion exchange material" refers to a solid phase that is negatively charged (i.e., a cation exchange resin) or positively charged (i.e., an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

The term "solid phase" refers to a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g., controlled pore glass), poly(styrenedivinyl)benzene, polyacrylamide, ceramic particles and derivatives of any of the above.

A "cation exchange resin" refers to a solid phase, which is negatively charged, and which thus has free cations for exchange with cations in an aqueous solution passed over or through the solid phase. A negatively charged ligand attached to the solid phase to form the cation exchange resin may, e.g., be a carboxylate or sulfonate. A "mixed mode ion exchange resin" refers to a solid phase which is covalently modified with cationic, anionic, and hydrophobic moieties.

The term "anion exchange resin" refers to a solid phase which is positively charged, e.g., having one or more positively charged ligands, such as quaternary amino groups, attached thereto.

The term "buffer" refers to a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g., polypeptide or impurity) from an ion exchange material is meant to remove the molecule therefrom by altering the ionic strength of the buffer surrounding the ion exchange material such that the buffer competes with the molecule for the charged sites on the ion exchange material.

Embodiments described herein relate to kits for and methods of extracting a polypeptide or protein from a biological sample. Extracting a polypeptide or protein from a biological sample refers to the processing of a biological sample so as to make the polypeptide more accessible for measurement. By way of example, extracting a polypeptide or protein includes the liberation and/or solubilization of polypeptides from cells, microorganisms or organelles, e.g., by rupturing or solubilizing membranes, cell walls, envelopes, etc. to release polypeptides comprised or encased within, attached to and/or incorporated into the membranes, cell walls, envelopes, etc., and/or cleaving a polypeptide from a larger chemical moiety.

The extraction methods and kits described herein use an extraction reagent that includes perfluorooctanoic acid (PFOA) to solubilize polypeptides and proteins in a biological sample. PFOA is a synthetic, stable perfluorinated C8 carboxylic acid that is generally used in preparation of fluoropolymers, which are used in the manufacture of a wide variety of products, such as Teflon. It was found that PFOA efficiently solubilizes polypeptides and proteins including cell transmembrane proteins. Solubilization of polypeptides or proteins by PFOA in the methods described herein is comparable to sodium dodecyl sulfate (SDS) and, unlike SDS, is compatible with proteolytic digestion, e.g., trypsin digestion. PFOA can also be readily removed following extraction of the polypeptides or proteins from the biological sample, which allows the method to be used in shotgun proteomics and subsequent mass spectrometry analysis.

FIG. 1 illustrates an embodiment of an extraction method 10 described herein. The extraction method includes a first step 20 of contacting a biological sample that includes a plurality of polypeptide or proteins with an extraction reagent to form a solution of the biological sample and the extraction reagent. The extraction reagent can include an aqueous buffered solution of PFOA that is used to solubilize the polypeptides or proteins in the biological sample.

In some embodiments, the plurality of polypeptides can be from a cell or cell membrane. The plurality of polypeptides can be in a single cell, or a community of cells. The plurality of polypeptides can include proteomes from the cell. Proteomes are a set of proteins expressed by the genetic material of an organism under a given set of environmental conditions.

In other embodiments, the biological sample can include environmental samples (e.g., water, food, sludges filtered from water or air, environmental wipes, etc.), serum, plasma, blood, synovial fluid, cerebrospinal fluid, sebaceous discharges, pus, mucous membrane secretions, lavage, etc.

In still other embodiments, the biological sample can be a clinical sample that contains pathogenic organisms. The sample may be collected by swabbing or washing a membrane or by removing fluid secreted from an s membrane. The sample is collected from a patient using a sampler (e.g., aspirator, swab, suction, or scrape), preferably by a swab (e.g., a nasal, nasal-pharyngeal, pharyngeal or genital swab) or a wash (e.g., a nasal or pharyngeal wash). In another specific embodiment, the sample is concentrated or cultured to increase the cellular or viral particle count.

The biological sample can be provided in a sample container or tube for extraction and the aqueous buffered solution of PFOA can be added to the sample tube to facilitate solvation of the polypeptides in the biological sample. The aqueous buffered solution of PFOA can include a concentration or amount PFOA effective to solubilize polypeptides in the biological sample. In some embodiments the amount of PFO in the extraction reagent can be up to about 2% w/v of the solution or extraction reagent. The aqueous buffered solution of PFOA can be buffered with a salt, such as ammonium bicarbonate.

After contacting the biological sample with the extraction reagent, the biological sample and the extraction reagent can be agitated by, for example, applying ultrasonic energy to the solution of the biological sample and the extraction reagent, to dissolve to the biological sample.

Optionally, following or concurrently with contacting the biological sample with the extraction reagent, the biological sample can be contacted with at least one denaturing agent to denature polypeptides or proteins solubilized by the extraction reagent. In one embodiment, the denaturing agent can include a reducing agent having an ability of reducing disulfide bonds and an s-alkylating agent. The at least one of a reducing agent and an s-alkylating can be provided in the extraction reagent when applied to the biological sample or applied to the biological sample in a separate solution.

The reducing agent can include any reducing agents having an ability of reducing disulfide bonds, though not specifically limited thereto, tritethyl phosphine (TEP), DTT, GSH, bME, TCEP, cysteine, mercaptoethylamine and mercaptopropionate. The alkylating agent can include 2-iodoethanol, iodoacetic acid and iodoacetic acid amide, as well as acetic acid 2-bromoethyl ester, (S)-(+)-2-amino-4-bromobutyryl hydrobromide, bromoacetaldehyde diethyl acetal, 2-bromoacetamide, bromoacetic acid t-butyl ester, bromoacetic acid methyl ester, bromoacetonitrile, allyl bromide, 2,2-bis(bromomethyl)-1,3-propanediol, bromoacetaldehyde dimethyl acetal, bromoacetic acid, bromoacetic acid ethyl ester, bromoacetone, 4-(bromoacetylamino)benzoic acid, 4-(bromoacetyl)morpholine, 4-bromo-2-butanesulfonic acid sodium salt, 4-bromo-1-butanol, 4-bromo-1-butene, 2-bromo-N-tert-butyl-3,3-dimethylbut-ylamide, 4-bromo-n-butyric acid, 3-bromobutyronitrile, 3-bromo-2-(bromomethyl)propionic acid, 1-bromo-2-butanol, 1-bromo-2-butanone, 4-bromobutyl acetate, 2-bromo-n-butyric acid, a-bromo-.gamma.-butyrolactone, 4-bromobutyronitrile, ((1R)-(endo, anti))-(+)-3-bromocamphor-8-sulfonic acid ammonium salt, (1S)-(+)-3-bromocamphor-10-sulfonic acid hydrate, 2-bromo-2-cyano-N,N-dim-ethylacetamide, 2-bromoethanesulfonic acid sodium salt, 2-bromoethylamine hydrobromide, 4-(2-bromoethyl)benzoic acid, 2-bromoethyl methyl ester, (+)-3-bromocamphor-8-sulfonic acid ammonium salt, bromocholine bromide, 1-bromo-2,2-dimethoxypropane, 2-bromoethanol, 4-(2-bromoethyl)benzenesulfonic acid, 2-(2-bromoethyl)-1,3-dioxane, 2-bromoethylphosphonic acid diethyl ester, 2-bromoisobutyric acid, 2-bromomalonamide, 2-(bromomethyl)acrylic acid, 2-bromomethyl-1,3-dioxolane, 2-(bromomethyl)-2-(hydroxymethyl)-1,3-propanediol, bromonitromethane, a-bromophenylacetic acid, 2-bromoisovaleric acid, bromomalonic acid diethyl ester, 4-(bromomethyl)benzoic acid, 5-bromo-1-methylhydantoin, 4-bromomethylphenylacetic acid, 2-bromo-2-nitro-1,3-propanediol, 3-bromo-1,2-propanediol, 3-bromopropanesulfonic acid, 1-bromo-2-propanol, 3-bromopropionaldehyde diethyl acetal, 2-bromopropionamide, 2-bromopropionic acid, 2-bromopropionitrile, 3-bromopropylamine hydrobromide, 3-bromopropanesulfonic acid sodium salt, 3-bromo-1-propanol, 3-bromopropionaldehyde dimethyl acetal, 3-bromopropionamide, 3-bromopropionic acid, 3-bromopropionitrile, (3-bromopropyl) phosphonic acid, (3-bromopropyl)trimethylammonium bromide, 3-bromopyruvic acid hydrate, 2-bromo-1,1,1-triethoxypropane, 2-bromo-n-valeric acid, dibromoacetonitrile, epibromohydrin, N-methylsulfonyl-3-bromopropionamide, 3-bromopyruvic acid, bromosuccinic acid, 11-bromoundecanoic acid, bromovalerylurea, 2,3-dibromo-1-propanol, ethyl bromopyruvate, tetrahydrofurfuryl bromide, N-(3-carboxyethyl)maleam-idic acid, cis-aconitic acid, acrylic acid 2-carboxyethyl ester, fumaric acid monoethyl ester, maleic acid, maleic acid monoamide, maleic acid monomethyl ester, N-(3-carboxypropyl)maleamidic acid, acrylic acid, acrylonitrile, 2-(acryloylamino)isobutyric acid, itaconic acid, maleic acid disodium salt, maleic acid monoethyl ester, N-methyl-(maleic acid monoamide), 2-acrylamido-2-methylpropanesulfonic acid, 2-aminoethyl hydrogensulfate, (2-bromoethyl) methyl sulfate, 1,4-butanesultone, 1,2:5,6-di-O-isopropylidene-3-O-(methylsulfonyl)-.alpha.-D-glucofuranose, 2,2-dimethyl-1,3-dioxolan-4-ylmethyl p-toluenesulfonate, methacrylic acid 3-sulfopropyl ester potassium salt, (2-(acryloxy)ethyl)trimethylammonium methylsulfate, benzenesulfonic acid 2-methoxyethyl ester, 1,3-butanediol cyclic sulfate, cyanomethyl benzenesulfonate, dimethyl (4S,5S)-1,3,2-dioxathiolane-4,5-dicarboxylate 2,2-dioxide, 1,3,2-dioxathiolane 2,2-dioxide, (2-(methacryloyloxy)ethyl)trimethylammon-ium methylsulfate, N-(2-iodoethyl)-trifluoroacetamide, iodomethane, 2-iodoacetamide, iodoacetonitrile, 3-iodopropionic acid, sodium iodoacetate, iodoacetic acid, 4-iodobutyric acid, 3-iodopropanesulfonic acid sodium salt, lithium iodoacetate, methanesulfonic acid ethoxycarbonylmethyl ester, 2-methylpropane sultone, 1,3-propanediol cyclic sulfate, propargyl benzenesulfonate, tetraethylene glycol monooctyl ether methanesulfonate, p-toluenesulfonic acid pentafluorobenzyl ester, p-toluenesulfonic acid 2-(2-n-propoxyethoxy)ethyl-1 ester, methanesulfonic acid 2-methoxyethyl ester, methylpropane sultone, propane sultone, 3-sulfopropyl acrylate potassium salt, p-toluenesulfonic acid 2-ethoxyethyl ester, p-toluenesulfonic acid propargyl ester, 2-(p-toluenesulfonyl)ethanol, 5'-tosyladenosine, aziridine-2-carboxylic acid methyl ester, ethyleneimine, propyleneimine, 1-(2-hydroxyethyl)ethyl-eneimine, 4-vinylpyridine, vinylsulfonic acid sodium salt, monoethyl fumarate potassium salt, propiolic acid, trans, trans-muconic acid, maleimide, N-methylmaleimide, N-ethylmaleimide, N-hydroxymaleimide, N-carbamoylmaleimide and 3-maleimidopropionic acid.

It will be appreciated that other polypeptide or protein denaturing agents can be used as long as the denaturing agent does not adversely affect the yield of the isolated proteins or polypeptides and/or subsequent analysis by, for example, mass spectrometry.

Following extraction of the polypeptides with the extraction reagent, the polypeptides can optionally be precipitated using a mixture of cold acetone. The cold acetone solubilize lipids from the sample, which can then be removed. The precipitated polypeptides can be centrifuged to from a pellet further washed with acetone and then redissolved in an extraction reagent comprising an aqueous buffered solution of PFOA.

After contacting the biological sample with the extraction reagent and, optionally, denaturing the polypeptides and precipitating the denatured polypeptides, at step 30, the solution of extracted polypeptides and extraction reagent can then be contacted with a proteolytic enzyme to promote polypeptide or protein digestion. The proteolytic enzymes can include, for example, ProK, pronase, pepsin, trypsin, chymotrypsin, carboxypeptidase and elastase. In certain embodiments, the proteolytic enzyme can include trypsin. In some embodiments, the solution of the extracted polypeptides and the extraction reagent can be diluted with aqueous buffer prior to or currently with the addition of the proteolytic enzyme so that the PFOA concentration in the solution is about 0.1% to about 0.5% w/v of the solution. Advantageously, it was found that proteolytic enzymes, such as trypsin, retained fully enzymatically activity in PFOA concentrations up to 0.25%, and more than 80% of its activity in 0.5% PFOA. In contrast, trysin retained only about 10% activity at 0.5% SDS.

Following proteolytic digestion, at step 40, the extraction reagent including the PFOA can be readily removed from the solution of extracted polypeptides and extraction reagent by, for example, evaporation, chromatography, and/or solid phase extraction. In one embodiment, the extraction reagent including the PFOA can be removed by drying the solution of the extracted polypeptides and PFOA under low pressure (e.g., less than 10 mTorr) or vacuum at ambient temperature (e.g., 25° C.) or an elevated temperature (e.g., 60° C.). The dried digest can further be subjected to reconstitution using a polypeptide solvent (e.g., ethanol:ethylacetate:water:TFA (0.33:0.33:0.33:0.01, v/v/v/v) and subsequent evaporation (e.g., in aspeed-vac concentrator at 25° C. under low pressure of <10 mTorr) to remove trace amounts of PFOA. Advantageously, removal of the solvents and extraction reagent including PFOA by evaporation results in little (e.g., less than 5%, less than 1%, or less than 0.1%) to no loss polypeptides, proteins, or peptides from the original biological sample.

In other embodiments, the extraction reagent including the PFOA can be readily removed from the solution of extracted polypeptides and extraction reagent by, for example, chromatography, and/or solid phase extraction. As shown in example 2, the extraction reagent can be removed using at least one of strong cation exchange chromatography, hydrophilic interaction chromatography, fluorous solid phase extraction, or anion exchange chromatography. Strong cation exchange chromatography, hydrophilic interaction chromatography, and fluorous solid phase extraction can remove PFOA efficiently. However, strong cation exchange chromatography and hydrophilic interaction chromatography have a lower peptide recovery than the fluorous solid phase extraction chromatography. The strong cation exchange chromatography and hydrophilic interaction chromatography procedures of removing PFOA are much faster (<10 min) than the evaporation method although peptide recovery is lower compared to evaporation. The peptide recovery rates can be improved using an online strong cation exchange chromatography or hydrophilic interaction chromatography coupled to reverse-phase LC-MS/MS. Peptide elution fractions from both the chromatographic methods are compatible with reverse-phase chromatography.

The peptides isolated by extraction and removal of the extraction reagent, can be analyzed and/or quantified using an analytical technique, such as mass spectrometry (e.g., LC-MS/MS). Any mass spectrometer may be used to analyze the peptides or proteins. For example, the mass spectrometer may be a Matrix-Assisted Laser Desorption/Ionization ("MALDI") Time-of-Flight ("TOF") Mass Spectrometer, available from PerSeptive Biosystems, Framingham, Mass.; an Electrospray Ionization ("ESI") ion trap mass spectrometer, available from Finnigan MAT, San Jose, Calif.; or an ESI quadrupole mass spectrometer, available from Finnigan MAT or the Perkin-Elmer Corporation, Foster City, Calif.

In some embodiments, the mass spectrometry may be carried out at least in part using shotgun proteomics. In other embodiments, shotgun proteomics can be carried out using all or any portion of the steps described above with regard to extracting the polypeptides from biological sample, such as a cell population. In one embodiment, shotgun proteomics can be carried out on an extracted cell lysate without the need to use chromatography. The extracted cell lysate can be whole cell lysate or a fraction of the whole cell lysate (e.g., extracted plasma membrane). Although shotgun proteomics can be used to avoid the use of chromatography, chromatography may be used in combination with shotgun proteomics if desired.

The mass spectrometry data can be used to identify the types and relative abundance of proteins, polypeptides, or peptides in the sample. Proteomic databases and algorithms that use mass sepctrometery data to identify specific proteins are known.

Embodiments of the application also relate to a kit for polypeptides from a biological sample. The kit can include, in one or more containers an extraction reagent that includes a aqueous buffered solution of PFOA. In some embodiments, the perfluorooctanoic acid can be provided in the extraction reagent at concentration of up to 2% w/v perfluorooctanoic acid. The extraction reagent can further include reagents for reduction and alkylation of cysteine residues (e.g., triethyl phosphine and iodoethanol), a proteolytic enzyme or protease, such as trypsin, and a column, such as a strong cation exchange chromatography column, hydrophilic interaction chromatography column, and/or fluorous solid phase extraction column, which can remove PFOA efficiently.

The invention is further illustrated by the following examples.

Example 1

We have been in search of an ideal surfactant that can effectively solubilize hydrophobic proteins, is compatible with proteases, and can easily be removed from the samples prior to mass spectrometry analysis. We tested two volatile surfactants, pentafluorooctanoic acid (PFOA, CAS Registry No.: 335-67-1) and N,N-dihexylamine (CAS Registry No.: 143-16-8) whose boiling points are 188.0 and 193.5° C. at 760 Torr, respectively. Since PFOA was superb at efficiently solubilizing proteins compared to dihexylamine, we focused on PFOA. PFOA is a synthetic, stable perfluorinated C8 carboxylic acid that is generally used in preparation of fluoropolymers, which are used in the manufacture of a wide variety of products such as nonstick surfaces on cookware (Teflon) and protective finishes on carpets and clothing. Other applications include aerospace, automotive, chemical processing, semiconductor manufacturing, information, and telecommunication. Fluorinated surfactants have also been used by various laboratories to solubilize membrane proteins.

In this example, we show that PFOA efficiently solubilizes membrane proteins and is compatible with trypsin. By utilizing this volatile surfactant and denaturing proteins by the reduction and S-alkylation of cystine residues using volatile reagents, we developed a single-tube shotgun proteomics method. The detailed experimental workflow is described and the applicability of the method is demonstrated by analyzing a membrane preparation from photoreceptor outer segments.

Materials and Methods

Materials

PFOA was purchased from TCI America (Portland, Oreg.). Oxygen-18 enriched water was obtained from Isotec (Miamisburg, Ohio). Sequencing-grade, modified, porcine trypsin was purchased from Promega (Madison, Wis.). All other chemicals and materials were either reagent grade or of the highest quality commercially available.

Preparation of Photoreceptor Outer Segments Membrane Pellet

Bovine retinas obtained from WL Lawson Company (Omaha, Nebr.) were used to prepare the photoreceptor outer segment (OS) by sucrose density ultracentrifugation. All solvents used for bovine OS preparations contained protease inhibitors (1 mM EDTA, 0.2 mM PMSF, 0.7 µg/µL leupeptin, and 0.5 µg/µL pepstatin A) to inhibit protein degradation and 100 µM diethylenetriamine pentaacetic acid (DTPA) to inhibit oxidation. After the OS were isolated, the purified OS solution (10 µL) was mixed with 100 µL of 100 mM ammonium bicarbonate (ABC) that contained the protease inhibitors, centrifuged at 15,000 g for 10 minutes, and then the supernatant was discarded. The precipitated OS membrane pellet was washed twice with 100 µL of 100 mM ABC and used for the proteomic analysis described below.

Protein Solubilization Efficiencies of Various Solubilizing Agents

The protein solubilization efficiencies of different solubilizing agents were studied by solubilizing the OS membrane protein pellet in 50 µL of 100 mM ABC containing either 1% SDS (w/v), 1% PFOA (w/v), 4 M urea, or 4 M guanidine-HCl (Gdn-HCl). The solubilized pellet solution was sonicated with a VirSonic 100 ultrasonic cell disrupter (SP Scientific, Gardiner, N.Y.) three times at 4.5 kHz of ultrasonic frequency for 9 seconds with 3-minute intervals between the sonications. The resulting protein extract was centrifuged at 15,000 g for 10 minutes, and the solubilized proteins in the supernatant were quantified using a DC protein assay kit (Bio-Rad, Hercules, Calif.).

Effect of PFOA on Trypsin Activity

To measure the amidase activity of 100 nM trypsin, we tracked the hydrolysis of 2 mM Ac-Lys-p-nitro aniline hydrochloride through absorbance increase at 405 nm over 3 min in 100 mM ABC using an ELISA plate reader (Thermo-Fisher Scientific, Waltham, Mass.). The enzyme activity observed in the absence of solubilizing agents was the control and was considered 100%. The activity in the presence of different concentrations of surfactant (SDS or PFOA) or chaotropic agents (urea or Gdn-HCl) was expressed with respect to the control under the same experimental conditions.

Single-Tube Proteolytic $^{18}O$ Labeling

Figure 2:
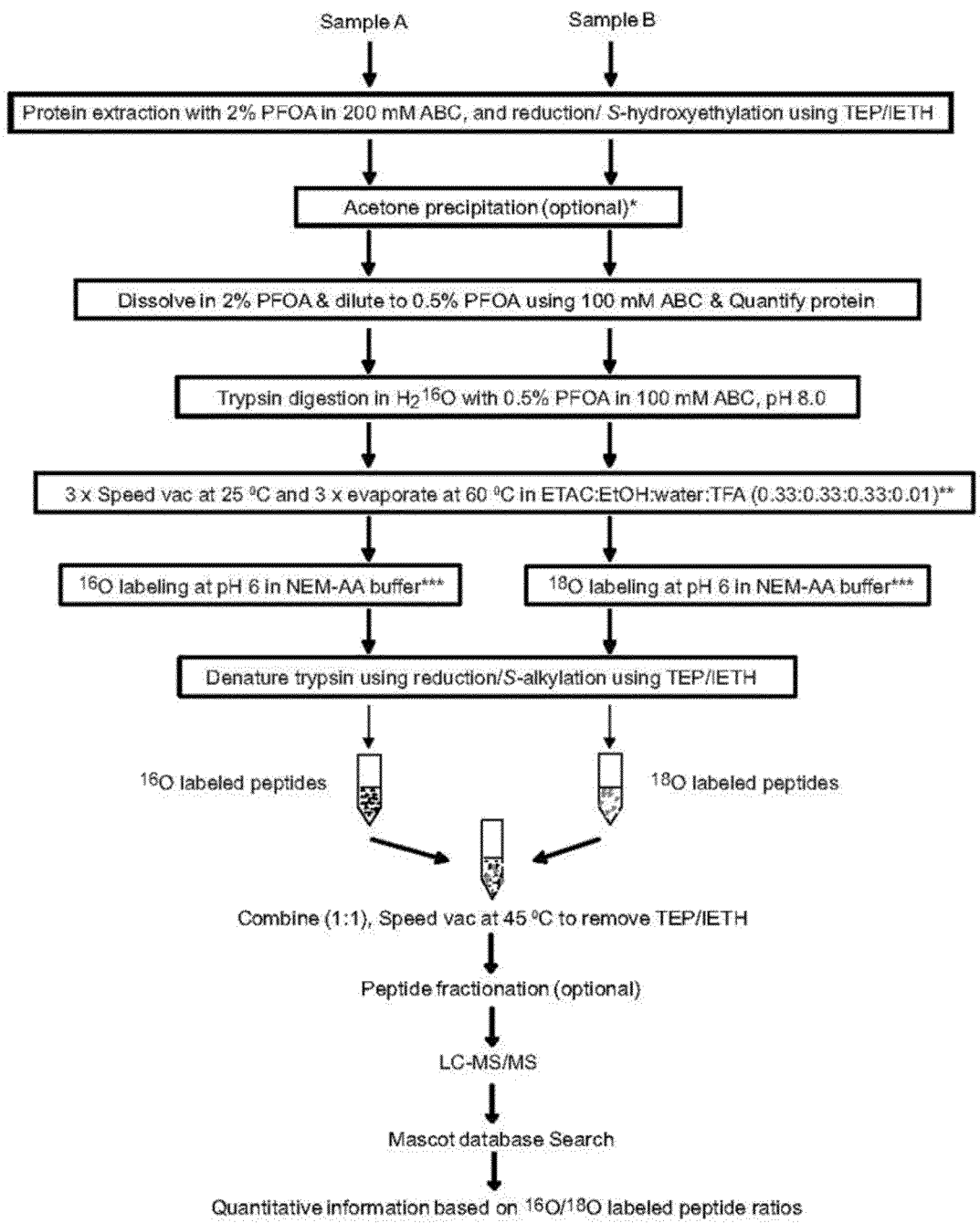
FIG. 2 is a flow diagram illustrating an extraction method in accordance with another embodiment.

The entire experimental workflow of a single-tube proteolytic $^{18}O$ labeling is shown in FIG. 2. In this hypothetical proteomic experiment, two identical OS membrane pellets from 10 μL of OS solution in 1.5-mL low retention tubes (Fisher Scientific, Pittsburgh, Pa.) were dissolved in 50 μL of 2% PFOA in 200 mM ABC by applying ultrasound energy at 4.5 kHz three times for 9 seconds with a 3-minute pause between the strokes. The extracted OS membrane proteins were reduced with 21 mM triethyl phosphine (TEP) at 45° C. for 1 hr and then S-alkylated by 58 mM iodoethanol (IETH) at 45° C. for 2 hr in the dark. Then, the proteins were precipitated by mixing with a 6-fold excess volume of ice-cold acetone and incubated 2 hr at −20° C. The acetone precipitation removes lipids from the protein sample. The precipitated proteins were then centrifuged at 2400 g for 10 minutes in a table-top centrifuge, and the pellet was washed twice with ice-cold acetone. The protein pellet was air dried for 10 minutes, and then redissolved in 50 μL of 2% PFOA in 200 mM ABC by sonication in a water bath for 10 mM in a Bransonic Ultrasonic 2510R-MT (Danbury, Conn.). The protein solution was then diluted in 100 mM ABC to 0.5% PFOA, and the amount of dissolved protein was determined by the DC protein assay kit (Bio-Rad, Hercules, Calif.). A total of 25 μg protein in 200 μL of 0.5% PFOA in both the tubes was digested in $H_2$ $^{16}O$ by trypsin (1:100 substrate to protein ratio w/w) at 37° C. for 18 h. Following the digestion, the digest was dried in a speed-vac concentrator (Thermo-Fisher Scientific Model SPD121P-120) at 25° C. under low pressure of <10 mTorr. The dried digest was subjected to three cycles of reconstitution in 100 μL of ethanol:ethylacetate:water:TFA (0.33:0.33:0.33:0.01, v/v/v/v) and evaporation in the speed-vac concentrator at 25° C. under low pressure of <10 mTorr, followed by another three cycles of reconstitution in 100 μL of ethanol:ethylacetate:water:TFA (0.33:0.33:0.33:0.01, v/v/v/v) and evaporation in a speed-vac concentrator at 60° C. under atmospheric pressure (without applying vacuum). It should be noted that the concentrator rotor still needs to be rotated during the evaporation process at the atmospheric pressure to minimize adsorption of the peptides to the tube. After every reconstitution step the sample was sonicated in a water bath for 10 sec. The 100 μL solution was completely dried typically in 60 min. The six cycles of solubilization and evaporation procedure was needed to thoroughly remove the PFOA. Next, the peptides from each tube were dissolved in 25 μL of 100 mM N-ethylmorpholine-acetic acid (NEM-AA) buffer at pH 6 that was made with $H_2$ $^{16}O$ or $H_2$ $^{18}O$, respectively. The peptides were then incubated with trypsin (1:50 trypsin to peptide ratio w/w) at 25° C. for 18 hr to incorporate $^{16}O$ and $^{18}O$, respectively, into the carboxyl termini of the peptides. After the labeling, 75 μL of pure isopropyl alcohol was added to denature the trypsin, and the solutions were adjusted to approximately pH 8 by adding 1 M ABC dissolved either in $H_2$ $^{16}O$ or $H_2$ $^{18}O$. The trypsin was then inactivated completely by reduction with 21 mM TEP at 45° C. for 1 hr followed by S-alkylation by 58 mM IETH at 45° C. for 2 hr in the dark. The resulting $^{16}O$ and $^{18}O$ labeled peptides were mixed in a 1:1 ratio and all the volatile reagents were then removed in a Speed-vac concentrator at 45° C., and 1 μg of the mix was analyzed by LC-MS/MS.

TEP and IETH stock solutions were prepared in pure acetonitrile. All operations with PFOA removal by evaporation under atmospheric pressure needs to be performed in fume hood for safety reasons. NEM-AA buffer in $H_2$ $^{18}O$ was prepared by mixing 491 μL $H_2$ $^{18}O$, 2.95 μL glacial acetic acid and 6 μL of NEM. The pH of this solution becomes around 6. When greater than 200 μg of protein samples are processed, we recommend to use a larger sample tube and larger volume of the reconstitution solution (ethanol:ethylacetate:water:TFA).

LC-MS/MS Analysis

LC-MS/MS analyses used a UltiMate 3000 LC systems (Dionex Inc., San Francisco, Calif.) interfaced to a LTQ-Orbitrap XL mass spectrometer (Thermo-Finnigan, Bremen, Germany). The platform was operated in the nano-LC mode using the standard nano-ESI API source fitted with a PicoTip emitter that had an uncoated fitting and 10-μm spray orifice (New Objective, Inc., Woburn, Mass.). The solvent flow rate through the column was maintained at 300 nL/min using a 1:1000 splitter system. The protein digest (typically 5 μL) was injected into a reversed-phase C18 PepMap trapping column of 0.3×5 mm with a 5-μm particle size (Dionex Inc.) equilibrated with 0.1% formic acid/2% acetonitrile (v/v). It was washed for 5 min with the equilibration solution at a flow rate of 25 μL/min by using an isocratic loading pump operated through an auto sampler. Next, the trapping column was switched in-line with a reversed-phase C18 Acclaim PepMap 100 column of 0.075×150 mm (Dionex Inc.) and the peptides were chromatographed using a linear gradient of acetonitrile from 6% to 50% in aqueous 0.1% formic acid over 50 minutes at the 25 μL/min flow rate. The eluate was directly introduced to the mass spectrometer. The mass spectrometer was operated in a data-dependent MS to MS/MS switching mode, with the five most intense ions in each MS scan subjected to MS/MS analysis. The full MS scan was performed at a resolution of 60,000 in the Orbitrap detector and the MS/MS scans were performed in the ion trap detector in collision-induced dissociation (CID) mode. The threshold intensity for the MS/MS trigger was always set at 1000. The fragmentation was carried out using the CID mode with a normalized collision energy of 35. The data was entirely collected in the profile mode for the full MS scan and the centroid mode for the MS/MS scans. The dynamic exclusion function for previously selected precursor ions applied the following parameters: repeat count of 2, repeat duration of 45 seconds, exclusion duration of 60 seconds, and exclusion size list of 150. Xcalibur software (version 2.0.7, Thermo-Finnigan Inc., San Jose, Calif.) was used for instrument control, data acquisition, and data processing.

Protein Identification

Proteins were identified by comparing all of the experimental peptide MS/MS spectra to the Swiss-Prot (version 57) database using Mascot database search software (version 2.1.04, Matrix Science, London, UK). The S-hydroxyethylation of cysteine was set as a fixed modification while the oxidation of methionine to methionine sulfoxide and the modification of C-terminal with $^{18}O$ were variable modifications. The mass tolerance was set to 10 ppm for the precursor ion and to 0.8 Da for the product ion. Strict trypsin specificity was applied, allowing for two missed cleavages. Only peptides with a minimum score of 20 were considered significant. Scaffold software (Version Scaffold-2_06_00, Proteome Software, Inc., Portland, Oreg.) was used to validate MS/MS-based peptide and protein identification. Peptide identifications were accepted if they could be established at an ion score greater than 20 as specified by the Peptide Prophet algorithm. Protein identifications were accepted if they could be established at greater than 95% probability and contained at least two identified peptides. Protein probabilities were assigned by the Protein Prophet algorithm.

Calculation of $^{16}O/^{18}O$-Peptide Ratio

In-house software (Relative Quantification O18.2.2.2) employing a least-squares regression algorithm was used for the calculation of $^{16}O/^{18}O$ peptide ratios. This software plots 16O/18O-peptide intensities of all peptides identified from the same protein, and the slope of the linear regression fit is used as a $^{16}O/^{18}O$ peptide ratio for that protein. Only proteins with $R^2 \geq 0.85$ and a linear regression F-probability greater than 0.85 are reported as quantified proteins. Proteins with $R^2$ values or F-probabilities out of our range were manually investigated for possible peptide outliers. An obvious outlier was defined as a peptide whose removal changed the protein $R^2$ value by more than 0.2 or increased the F-probability to >0.85. If an obvious outlier was detected, it was removed from the peptide list. The slope of the linear regression fit was obtained from the plot of $^{18}O$ intensity on the y-axis vs. the $^{16}O$ intensity of the same peptide on x-axis. The slope value normalized the individual peptide ratios. This is expected to decrease the influence of experimental error (e.g., pipetting error during sample mixing) on the calculated ratios.

Results and Discussion

Protein Solubilization Efficiency of PFOA

The total protein amounts solubilized from the OS membrane protein pellet by various solubilizing agents are shown in Table 1. We found that 100 mM ABC could solubilize 9.2 µg of protein, 1% PFOA could solubilize 47.4 µg protein, and 1% SDS could solubilize 55.1 µg protein. So, PFOA and SDS solubilized over 5-fold more protein than 100 mM ABC. Surprisingly, Gdn-HCl solubilized only 7.3 µg and urea only 8.1 µg. These results demonstrate that PFOA can solubilize protein at an efficiency comparable to SDS, and considerably higher than urea and Gdn-HCl. The results also suggest that urea and Gdn-HCl may not help in solubilizing membrane proteins in proteomic applications. Because over 80% of the total weight of OS membrane protein is the seven-transmembrane receptor rhodopsin, the results should be considered most relevant for highly hydrophobic integral membrane proteins.

TABLE 1

Solubilization of membrane proteins by different reagents

| Solubilization agent | Protein amount solubilized (µg/10µ OS membrane preparation) |
|---|---|
| 100 mM ABC | 9.2 ± 2.0 |
| 25 mM SDS (0.8% w/v) | 55.1 ± 6.7 |
| 25 mM PFOA (1% w/v) | 47.4 ± 4.4 |
| 4M Urea | 8.1 ± 3.4 |
| 4M Gdn-HCl | 7.3 ± 4.1 |

Data are mean ± standard deviation from triplicate experiments

Effect of PFOA on the Trypsin Activity

Figure 3:
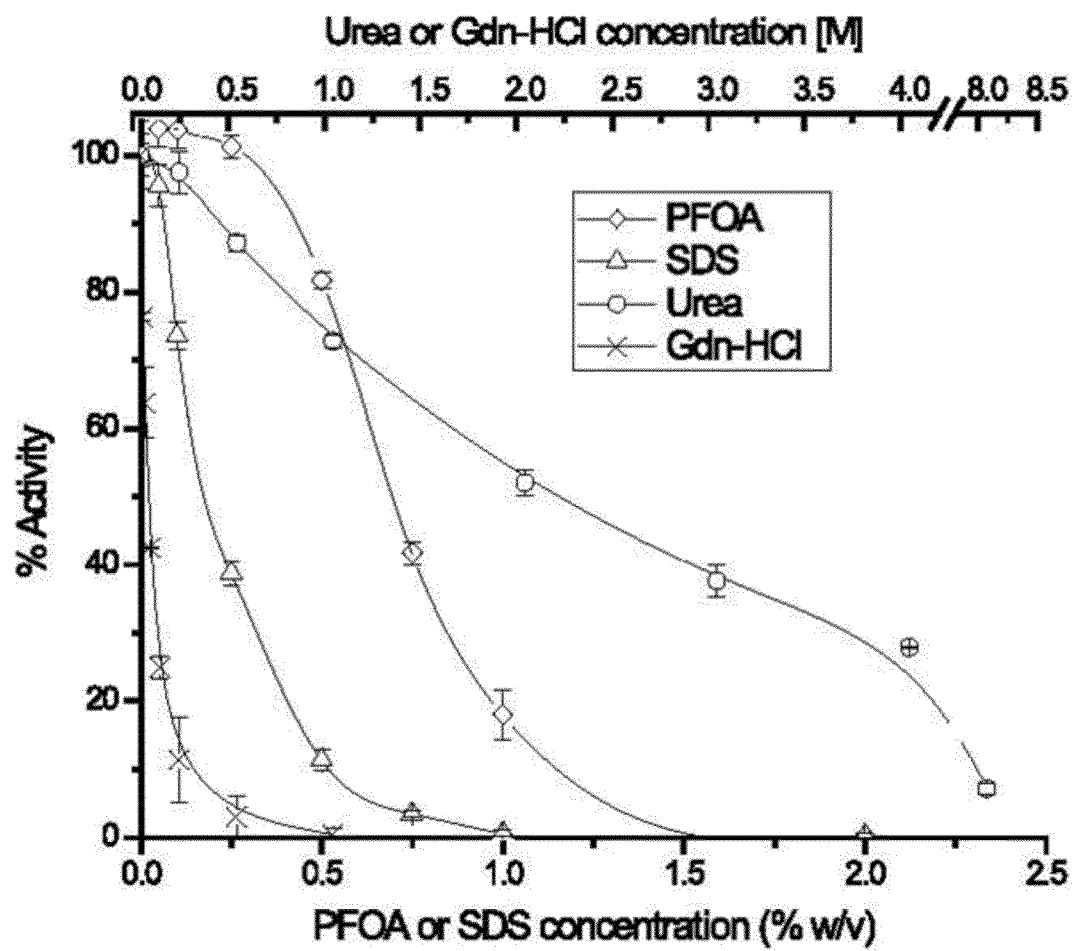
FIG. 3 illustrates a graph showing that different solubilizing agents affected the activity of trypsin. Each line in the graph represents the concentration dependent decrease in tryptic activity in the presence of various concentrations of PFOA (◊), SDS (Δ), urea (○), and Gdn-HCl (x).

We tested the activities of porcine trypsin in the presence of various concentrations of PFOA and compared the activity to other protein denaturation agents (FIG. 3). Trypsin retained full activity in PFOA concentrations up to 0.25%, and more than 80% of its activity in 0.5% PFOA. In contrast, trypsin retained only about 10% activity at 0.5% SDS. The results suggest that concentrations of PFOA below 0.5% can be used for protein digestion without drastically inhibiting the tryptic activity. The effect of urea and Gdn-HCl were also compared (FIG. 3). Trypsin retained approximately 50% of its activity in 2 M urea and 20% in 4 M urea, while it retained only 40% in 0.1 M Gdn-HCl and 20% in 0.25 M Gdn-HCl. These results were comparable to our previous report on porcine trypsin.

Removal of PFOA from Peptide Mixture

The major hurdle in the development of this method turned out to be the removal of PFOA from the peptide mixture after digestion. We initially tried removing PFOA from a tryptic digest of OS membrane proteins dissolved in 0.1% formic acid and 60% acetonitrile, which is a commonly used solvent mixture in proteomic applications. However, we were unsuccessful even after repeated evaporations in a speed-vac concentrator under low pressure of <10 mTorr. The peptide peaks broadened in LC-MS/MS (data not shown), suggesting that a considerable amount of PFOA remained with the peptide sample. We believe that the remaining PFOA molecules in the digest are mainly the ones interacting with peptides through ionic and/or hydrophobic interactions.

To remove PFOA completely from the peptide samples, we tested several factors including solvents, temperatures, and vacuum conditions that are likely to affect the evaporation process of PFOA. The solvents water, methanol, ethanol, ethyl acetate, acetonitrile, n-propanol, dimethyl formamide, and dimethylsulfoxide were tested individually and in mixes of various combinations and ratios. The temperatures of 30, 40, 50, and 60° C. and the pressures of 1 mTorr and 760 Torr were tested. A small quantity of TFA (1%) was included in all the solutions to protonate the carboxyl group of PFOA (the $pK_a$ value of PFOA is 3.8 at infinite dilution), which is expected to disrupt the ionic interactions between PFOA and peptides, therefore helps evaporating PFOA. A total of 50 µg of tryptic digest of bovine serum albumin (BSA) was dissolved in 100 µL of 0.1% v/v PFOA in the various solvents with 1% TFA. The PFOA was evaporated at the different temperatures and pressures. After the evaporation, the resulting BSA digest was redissolved in 0.1% formic acid and 50% acetonitrile, and analyzed by flow injection MS. The residual PFOA was measured by monitoring the extent of $(M-H)^-$ ion of PFOA (m/z 413). We found that the PFOA amount in the BSA digest was decreased below detectable level after three cycles of reconstitution in 100 µL of ethanol:ethylacetate:water:TFA (0.33:0.33:0.33:0.01, v/v/v/v) and evaporation at 60° C. under atmospheric pressure of 760 Torr (data not shown).

Figure 4:
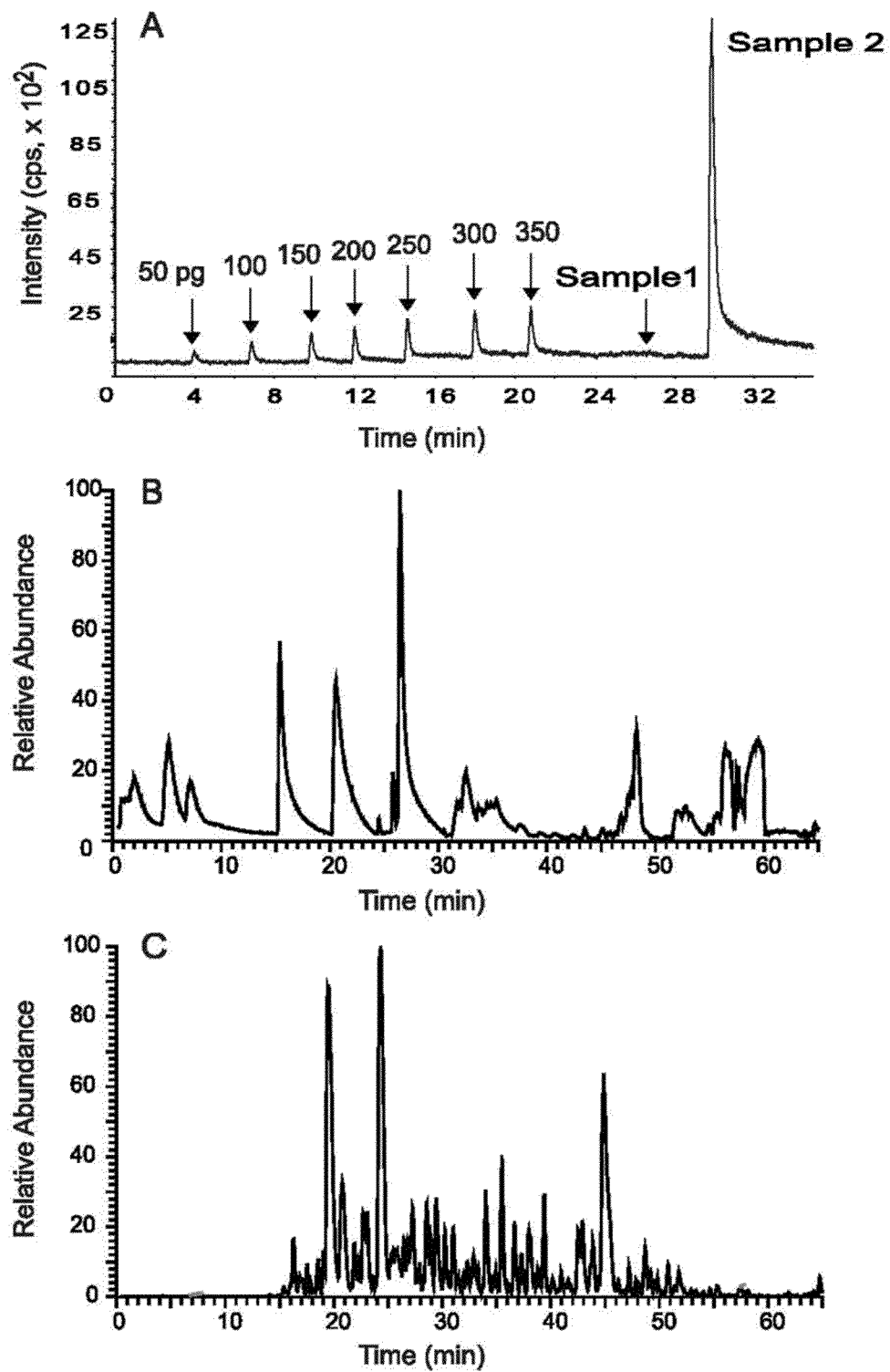
FIGS. 4(A-C) illustrate total ion current chromatograms of the tryptic digest of OS membrane proteins. (A) Residual PFOA in the tryptic digest of OS membrane proteins quantified by flow injection analysis. Different concentrations of the PFOA standard solution (50-350 pg) and samples in 1 μL of 0.1% formic acid and 50% acetonitrile were injected into a flowing carrier stream consisting of 0.1% formic acid and 50% acetonitrile at 40 μL/min that was directly connected to a mass spectrometer (QStar, Applied Biosystems, Foster City, Calif.) equipped with an electrospray ion source. The (M-H)$^-$ ion (m/z 413) of PFOA was monitored. An aliquot of the digest was analyzed by flow injection analysis after three cycles of evaporation in ethanol:ethylacetate:water:TFA (0.33:0.33:0.33:0.01, v/v/v/v) at 25° C. in a speed-vac concentrator under low pressure of <10 mTorr (Sample 2). The remaining digest was subjected to another three cycles of evaporation in ethanol:ethylacetate:water:TFA (0.33:0.33:0.33:0.01, v/v/v/v) at 60 uC in a speed-vac concentrator under atmospheric pressure of 760 Torr (Sample 1). (B) 1 μg of the digest from sample 2 analyzed by LC-MS/MS. (C) 1 μg of the digest from sample 1 analyzed by LC-MS/MS.

The digest of OS membrane protein (25 µg) in 200 µL of 0.5% PFOA in 100 mM ABC (total PFOA amount=1 mg) was subjected to speed-vac, and then three cycles of reconstitution in 100 µL of ethanol:ethylacetate:water:TFA (0.33:0.33:0.33:0.01, v/v/v/v) and evaporation in a speed-vac concentrator under low pressure of, 10 mTorr. An aliquot (2.5 µg) was redissolved in 50 µL of 0.1% formic acid and 50% acetonitrile, and 1 µL of which was analyzed by flow injection MS (FIG. 4A, Sample 2). The residual PFOA was estimated to be 12 µg, which corresponds to 1.2% of the initial amount. When 1 µg of the same digest was analyzed by LC-MS/MS, the peptide peak widths were broader than normal (FIG. 4B), suggesting that a small amount of PFOA remained in the digest can interfere with the chromatography. In order to remove the residual PFOA completely, the rest of the digest (22.5 µg) was subjected to another three cycles of reconstitution in 100 µL of ethanol:ethylacetate:water:TFA (0.33:0.33:0.33:0.01, v/v/v/v) and evaporation at 60° C. under atmospheric pressure of 760 Torr. An aliquot (2.5 µg) was redissolved in 50 mL of 0.1% formic acid and 50% acetonitrile, and 1 µL of which was analyzed by flow injection MS (FIG. 4A, Sample 1). As can be evident in the figure, PFOA was not detectable, suggesting the virtually complete removal of PFOA from the digest.

The PFOA free tryptic digest of OS membrane proteins (1 µg) was analyzed by LC-MS/MS (FIG. 4C). The peak broadening problem caused by PFOA was obviously fixed after the removal of PFOA. A total of 75 proteins were identified by at least two unique peptides from the single 1 hr LC-MS/MS run of the tryptic digest of OS membrane proteins, and 67% of these, or 50 proteins, were classified as membrane proteins. This result demonstrates the usefulness of PFOA for identifying membrane proteins in shotgun proteomics.

Single Tube Proteolytic $^{18}$O Labeling Method

Figure 5:
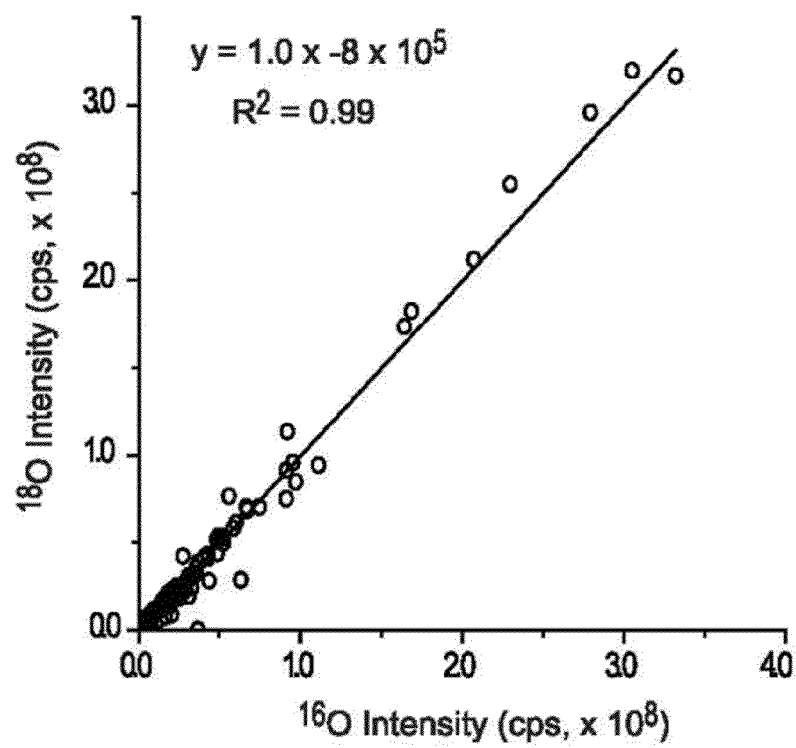
FIG. 5 illustrate a plot comparing the intensities of $^{16}$O- and $^{18}$O-labeled peptides. Linear regression analysis was performed on a total of 377 peptides. The equations and $R^2$ values for the regression line are shown.

Proteolytic $^{18}$O labeling is one of the most widely used quantitative shotgun proteomics methods, and it determines the relative ratios of individual proteins between two samples. In this method, protein digestion and $^{18}$O labeling, which are catalyzed by the same protease, can be decoupled. In a typical decoupled experiment, proteins are digested before being subjected to $^{18}$O labeling. Therefore, we attempted to incorporate the $^{18}$O labeling procedures into the protocol. The PFOA-free tryptic digests of the OS membrane proteins were reconstituted in NEM-AA buffer pH 6 made with either $H_2$ $^{16}$O or $H_2$ $^{18}$O (FIG. 2). The peptides were then incubated with trypsin to incorporate $^{16}$O or $^{18}$O into the carboxyl termini of the peptides. After the labeling, the trypsin was inactivated by using volatile reagents to reduce and alkylate its cystine residues. The $^{16}$O and $^{18}$O labeled peptide samples were mixed in 1:1 ratio and the excess reagents were removed in a speed-vac concentrator. When 1 µg of the mixed peptide sample was analyzed by LC-MS/MS, we quantified about 377 peptides. FIG. 5 plots the $^{16}$O-versus $^{18}$O-labeled peptide intensities observed in the LC-MS/MS and shows the regression line ($R^2$=0.99) from linear regression analyses. This result demonstrates that $^{18}$O labeling can be successfully performed in a single tube. This single-tube, quantitative, shotgun proteomics method does not require proteomic samples to be transferred out of the original reaction tube until the $^{18}$O labeling is completed, which limits the loss of samples only to the tube used and thus assures high recovery of the peptides from minute quantities of tissue samples.

Advantages and Drawbacks of the Single-Tube Proteolytic $^{18}$O Labeling Method The highly efficient protein solubilization of our PFOA method is comparable to SDS, the gold standard surfactant for protein solubilization. The volatile nature of all the solvents, reagents, and buffers used in the method allows them to be removed by evaporation. This evaporation means we expect no loss of proteins or peptides prior to mass spectrometry analysis except loss of the peptides due to the adsorption on the tube used during the sample preparation, assuming that no proteins or peptides are volatile unless derivatized. This method would be especially valuable when available sample amounts are limited. After PFOA was removed from protein digests, we have successfully fractionated peptides by strong cation exchange chromatography and by alkaline-pH reverse-phase chromatography (unpublished results), therefore such peptide fractionation methods can be incorporated into the method. This evaporation process could be accelerated by finding a better solvent(s) from which PFOA can be efficiently evaporated at a low pressure of <10 mHg, which is the typical operation pressure of a speed-vac concentrator.

Example 2

This example is used to establish a rapid and efficient method for removing PFOA from the proteomic samples. We tested four chromatographic approaches, strong cation exchange (SCX) chromatography, hydrophilic interaction chromatography (HILIC), fluorous solid phase extraction (FSPE), and anion exchange (ANX) chromatography. We chose SCX chromatography because PFOA cannot be positively charged and therefore should not bind to the SCX resin. However, because the majority of peptides will bind to the resin when chromatographic pH conditions are acidic (pH<3), the bound peptides should be freed from the PFOA. HILIC was tested, because the HILIC has been successfully used to remove detergents, including SDS, from the protein digests. Since PFOA is nonpolar, we predict that PFOA does not bind to the HILIC resin; and, therefore, the bound peptides can be freed from PFOA. FSPE was tested because highly fluorinated molecules such as PFOA have been shown to bind strongly to fluorous silica gel, which should separate PFOA from the nonfluorous compounds. The FSPE technique has been employed in the proteomics field to enrich peptides that are labeled with fluorous tags. Finally, we tested ANX chromatography. The $pK_a$ of carboxyl group of PFOA in diluted solution has been determined experimentally to be 3.8. However, contrary to this, other reports have suggested that the $pK_a$ of PFOA is lower than 1. If the $pK_a$ of PFOA is truly lower than 1, PFOA should be well deprotonated under the pH>2.5, and therefore should be trapped by the ANX resin. In contrast, the majority of peptides will not bind to the ANX resin when chromatographic pH conditions are acidic (pH≈2.5).

Figure 6:
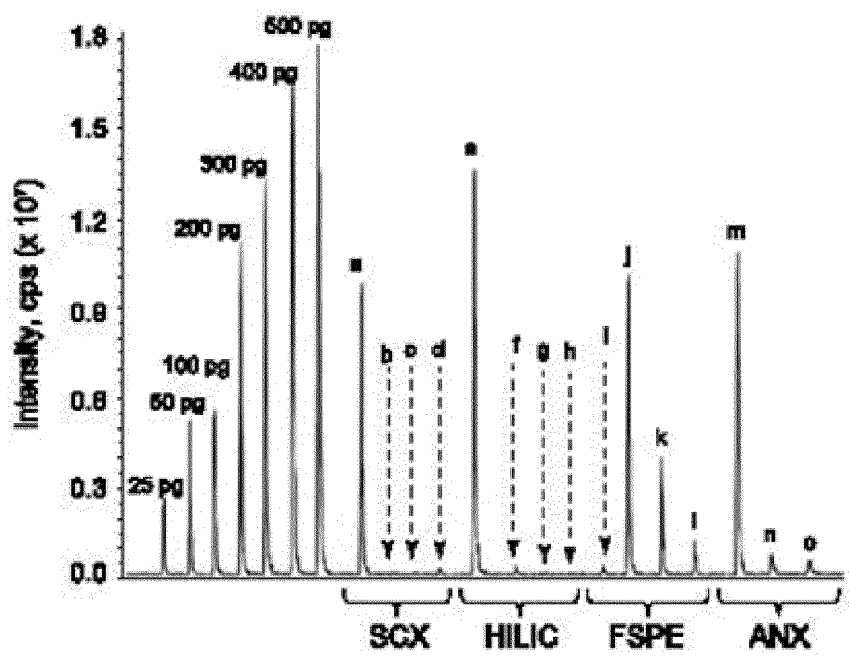
FIG. 6 illustrates a chart showing flow injection analysis of elution fractions from SCX, HILIC, FSPE, and ANX chromatography. Varying concentrations of the PFOA standard solution (25-500 pg) and samples in 0.1% formic acid, 50% ACN were injected into a flowing carrier stream directly connected to a mass spectrometer (0.1% formic acid, 50%

A tryptic digest of S-carbamidomethylated bovine serum albumin (BSA) in 50 mM ammonium bicarbonate containing PFOA (TCI America, Portland, Oreg., USA) was used as a test sample. The SCX UltraMicroSpin column (100-µL resin volume) (NestGroup, Southboro, Mass., USA) was equilibrated with 1-mL-equilibration buffer (5 mM ammonium formate containing 20% ACN pH 3.0). The column was loaded with 50 µg of BSA digest containing 200-µg PFOA in 400-µL equilibration buffer and flushed with 600-µL equilibration buffer (flow-through fraction). The column was then washed twice with 1-mL-equilibration buffer (washing fraction 1 and 2) before eluting the bound peptides. The bound peptides were eluted with 400 µL of 300 mM ammonium formate buffer, pH 3.0 containing 20% ACN (elution fraction). Aliquots of the flow through (1500 000th), washing (150 000th), and elution fractions (150 000th) were used for estimating the PFOA amount by flow injection analysis (FIG. 6) as described in the Supporting Information. As expected, PFOA did not bind to the SCX resin, but eluted into the flow-through fraction (FIG. 6, peak a). PFOA was not detected into the following two washing fractions (FIG. 6, peaks b and c). The high-salt elution fraction, which contains most of the peptides, contained only trace amount of PFOA that did not interfere with the further LC-MS/MS analysis (FIG. 6, peak d).

To investigate peptide recovery, the high-salt elution fraction was mixed with 50 µg of $^{18}$O-labeled BSA digest and an-alyzed by LC-MS/MS to determine the peptide recovery, where peptides recovered at 100% are expected to give 1:1 ratios in peak height between the $^{16}$O-peptides (eluted) and the $^{18}$O-peptides (spiked). The $^{18}$O-labeled BSA digest was prepared as described in the Supporting Information. Peptides were identified by comparing MS/MS spectra to the Swiss-Prot (version 57) database using Mascot database search software (version 2.1.04, Matrix Science, London, UK). In-house software (relative quantification 018.2.2.2) employing a least-squares regression algorithm was used for the calculation of $^{16}O/^{18}O$ peptide ratios. The measured $^{16}O/^{18}O$ ratio of each peptide was normalized with its $^{16}O/^{18}O$ ratio obtained from a control experiment where the $^{16}O$- and $^{18}O$-labeled digests were mixed in 1:1 ratio and analyzed by MS without running through the chromatography column.

The recovery rates of BSA peptides using SCX chromatography are shown in Table 2. We confidently identified 21 tryptic peptides. The recovery rates for 16 of the peptides (SEQ ID Nos: 1-16) ranged from 39% to greater than 95% and the average recovery rate was 65%. The recovery rate for five of the peptides (SEQ ID No: 17-21) was less than 10%. The peptides with lower recovery rates were predominately acidic peptides as indicated by the pI values in the table, which likely did not bind well to the SCX column and were lost in the flow-through fraction. Performing SCX chromatography in a more acidic pH environment (pH 2.5) did not improve peptide recovery (data not presented), presumably due to the partial protonation of the sulfopropyl group of the stationary phase. Additionally, no difference in peptide recovery was observed between digests with PFOA and without PFOA (data not presented), suggesting that low acidic peptide recovery rates resulting from SCX chromatography are independent of PFOA.

TABLE 2

Recoveries of BSA peptides from SXC, HILIC, and FSPE

| | | | | Peptide recovery (%) | | |
|---|---|---|---|---|---|---|
| SEQ ID No: | Peptide Sequence | M + H | pI | SCX | HILIC | FSPE |
| SEQ ID No: 1 | LVTDLTK | 789.5 | 5.8 | <95 | <10 | <10 |
| SEQ ID No: 2 | YIYEIAR | 927.5 | 6.0 | <95 | <10 | <10 |
| SEQ ID No: 3 | VPQVSTPTLVEVSR | 1511.8 | 6.0 | <95 | <10 | <10 |
| SEQ ID No: 4 | LVNELTEFAK | 1167.6 | 4.5 | <95 | <10 | <10 |
| SEQ ID No: 5 | KVPQVSTPTLVEVSR | 1639.9 | 8.8 | <95 | <10 | <10 |
| SEQ ID No: 6 | KQTALVELLK | 1142.7 | 8.6 | <95 | <10 | <10 |
| SEQ ID No: 7 | AEFVEVTK | 922.5 | 4.5 | 91 | <10 | <10 |
| SEQ ID No: 8 | RHPYFYAPELLYYANK | 2045.0 | 8.4 | 77 | <10 | <10 |
| SEQ ID No: 9 | RHPEYAVSVLLR | 1439.8 | 8.8 | 51 | <10 | <10 |
| SEQ ID No: 10 | LGEYGFQNALIVR | 1479.8 | 6.0 | 87 | 26 | 28 |
| SEQ ID No: 11 | SLHTLFGDELCK | 1419.7 | 5.3 | 79 | 59 | <10 |
| SEQ ID No: 12 | LKPDPNTLCDEFK | 1576.8 | 4.6 | 50 | 30 | <10 |
| SEQ ID No: 13 | DAFLGSFLYEYSR | 1567.7 | 4.4 | 48 | 31 | 36 |
| SEQ ID No: 14 | M(o)PCTEDYLSLILNR | 1740.8 | 4.4 | 40 | 13 | <10 |
| SEQ ID No: 15 | YNGVFQECCQAEDK | 1747.7 | 4.1 | 39 | 92 | 42 |
| SEQ ID No: 16 | TVMENFVAFVDK | 1399.7 | 4.4 | 39 | 35 | 31 |
| SEQ ID No: 17 | ECCHGDLLECADDR | 1753.7 | 4.1 | <10 | 86 | <10 |
| SEQ ID No: 18 | EYEATLEECCAK | 1506.6 | 4.1 | <10 | 34 | <10 |
| SEQ ID No: 19 | TCVADESHAGCEK | 1463.6 | 4.7 | <10 | >95 | <10 |
| SEQ ID No: 20 | ETYGDM(o)ADCCEK | 1494.5 | 3.9 | <10 | >95 | <20 |
| SEQ ID No: 21 | ETYGDMADCCEK | 1478.5 | 3.9 | <10 | 87 | 22 |

The poly(2-hydroxyethyl aspartamide)-silica packed HILIC UltraMicroSpin column (100 μL resin volume) (Nest Group) was equilibrated with 1 mL equilibration buffer (20 mM ammonium formate containing 80% ACN pH 3.0). The column was loaded with 50 μg of BSA digest containing 200 μg PFOA in 400 μL equilibration buffer and flushed with 600 μL equilibration buffer (flow-through fraction). The column was then washed twice with 1-mL-equilibration buffer (washing fraction 1 and 2) before eluting the bound peptides. The bound peptides were eluted with 400 μL of 20 mM ammonium formate buffer, pH 3.0 (elution fraction). Aliquots of the flow through (1 500 000th), washing (150 000th), and elution fractions (150 000th) were used for estimating the PFOA amount by flow injection analysis (FIG. 6). As expected, PFOA did not bind to the HILIC resin, but eluted mostly into the flow-through fraction (FIG. 6, peak e) with a trace quantity eluting into the following two washing fractions (FIG. 6, peaks f and g). The aqueous elution fraction, which contains most of the peptides, contained no PFOA (FIG. 6, peak h). The result shows that the flow-through fraction contains most of the PFOA that was loaded on the column, and the peptide-eluted fraction does not contain any PFOA (FIG. 6, peak h).

In contrast with the SCX chromatography, acidic peptides (SEQ ID NOs: 17-21) were recovered well from the HILIC, while the recoveries of basic peptides (SEQ ID Nos: 5, 6, 8, and 9) were poor (Table 2). It was found found that of the poorly recovered peptides have the pI values greater than 6. It has been shown that positively charged amino acids (Arg, Lys, and His) bind significantly tightly to poly(2-hydroxyethyl aspartamide) support than other amino acids. We, therefore, believe that those poorly recovered peptides bound to the column tightly and were not eluted from the column Eluting the bound peptides in the presence of 500 mM NaCl did not improve the recovery of those peptides (data not shown), suggesting no involvement of ionic interaction between the tightly bound peptides and the stationary phase.

FSPE was performed using a 5-μm FluoroFlash silica gel (Fluorous Technologies, Pittsburgh, PA, USA). The gel was suspended in methanol and manually packed into a stainless steel guard column (2×20 mm) (Idex Health Science, Oak Harbor, WA, USA). The column was equilibrated with a 1-mL equilibration buffer (0.1% formic acid, 60% methanol), loaded with 50 μg BSA digest containing 50 μg PFOA in 200-μL equilibration buffer, and then washed with 400 μL equilibration buffer (flow-through fraction). The flow rate was set constant at 100 μL/min using a syringe pump (Harvard Apparatus, Holliston, MA, USA). An aliquot (120 000th) of the flow-through fraction was analyzed by flow injection analysis to check for unbound PFOA (FIG. 6). Only trace amount of PFOA was detected in the flow-through fraction (FIG. 6, peak i), suggesting that PFOA was almost completely absorbed by the FSPE resin. To determine the methanol concentration at which PFOA is eluted from the FSPE column, the column was washed sequentially with 400 μL 0.1% formic acid, 70% methanol (washing fraction 1), 400 μL 0.1% formic acid, 80% methanol (washing fraction 2), and 400 μL 0.1% formic acid, 100% methanol (washing fraction 3). Aliquots of the washing fractions (1400 000th) were analyzed by flow injection analysis. The results indicated that washing fraction 1, with a methanol concentration of 70%, eluted over 40% of the total PFOA loaded onto the column (FIG. 6, peak j). Residual PFOA was eluted with washing fractions 2 and 3 containing 80% and 100% methanol, respectively (FIG. 6, peaks k and l). Therefore, methanol concentrations must be lower than 60% for PFOA to be retained in the column The column used here was sufficient to retain PFOA loads up to 200 μg. We also tested ACN as an organic component in the equilibration buffer; however, the PFOA was not well retained on the column, which led to PFOA leakage into the flow-through fraction, even at concentrations lower than 50% (data not shown).

None of the peptides had good recovery rates from the FSPE column (Table 1). Low peptide recovery was likely due to tight binding of peptides to the resin. Increasing the equilibration buffer methanol concentration from 60% to 70% improves peptide recovery rates in the flow-through fraction. However, the increase resulted in significant elution of PFOA from the column (FIG. 6), which can ruin the separation of peptides in the subsequent LC-MS/MS analyses. We also tested the equilibration buffer (10 mM ammonium formate, 60% methanol) that Brittain and co-workers used for enrichment of fluorous agent tagged peptides. However, PFOA was not well retained under their chromatographic conditions, probably due to the increased hydrophilicity of PFOA at a neutral pH caused by the deprotonation of the carboxyl group on PFOA.

The ANX UltraMicroSpin column (100 μL resin volume) (Nest Group) was equilibrated with a 1-mL equilibration buffer (5 mM ammonium formate containing 20% ACN pH 2.5). The column was loaded with 50 μg of BSA digest containing 200 μg PFOA in 400 μL equilibration buffer and washed with 600 μL equilibration buffer (flow-through fraction). The column was further washed twice with 1 mL equilibration buffer (washing fraction 1 and 2). Aliquots of the flow through (1500 000th), and washing fractions (150 000th) were used for estimating the PFOA amount. The results indicated that flow-through fraction contains 70% of the PFOA that was loaded on the column (FIG. 6, peak m). The rest of the PFOA was eluted out in the washing fraction 1 and 2 (FIG. 6, peaks n and o). Thus, the PFOA was not trapped by the ANX column and coeluted with peptides in the flow-through fraction.

In summary, this example shows that SCX, HILIC, and FSPE can remove PFOA efficiently. However, SCX and HILIC have the better peptide recovery than the FSPE chromatography. The SCX and HILIC procedures of removing PFOA are much faster (<10 min) than the evaporation method. However, low recovery of acidic peptides in SCX chromatography and basic peptides in HILIC is a drawback. The SCX and HILIC method could be used as an alternative to the evaporation method in applications where analyzing the entire set of peptides is not essential. Additionally, peptide recovery rates should improve using an online SCX and HILIC coupled to reverse-phase LCMS. Peptide elution fractions from both the chromatographic methods are compatible with reverse-phase chromatography.

Materials

Ammonium salt of perfluorooctanoic acid (PFOA) was purchased from TCI America (Portland, Oreg., USA). Oxygen-18 enriched water was obtained from Isotec (Miamisburg, Ohio, USA). Sequencing-grade modified porcine trypsin was purchased from Promega (Madison, Wis., USA). All other chemicals and materials used were either reagent grade or of the highest quality commercially available.

Preparation of BSA Digest and $^{18}O$ Labeling of Peptides

BSA (1 mg) was dissolved in 50 μL of 8 M urea in 100 mM ammonium bicarbonate (ABC), reduced with 1 mM dithioerithritol (DTT) at 37° C. for 1 hr, and then S-alkylated by 2.5 mM iodoacetamide (IAC) for 1 hr in the dark. The protein solution was then diluted 10-fold with 100 mM ABC and digested by trypsin in $H_2^{16}O$ (1:100 substrate to protein ratio w/w) at 37° C. for 18 h. Following the digestion, the digest was concentrated in a speed-vac to 50 μL and then the residual trypsin activity was arrested by incubating the digest with 1 mM DTT at 37° C. for 1 hr followed by incubation with 2.5 mM IAC for 1 hr. After that the tryptic digest was desalted on a C18 ultra micro spin column (The Nest group, Southborough, Mass., USA). The recovered peptides were stored at −20° C. until further use.

An aliquot (25 μg) of the above BSA digest was dried in a speed-vac and dissolved in 25 μL of 100 mM sodium citrate buffer pH 6.0 in $H_2^{18}O$. Then 1 μg of trypsin (dissolved in 100 mM sodium citrate buffer pH 6.0 in $H_2^{18}O$) was added and incubated at 37° C. for 18 hr to label the peptides with oxygen-18. After the labeling, the residual tryptic activity was arrested as follows. First, 10 mg of solid guanidine-HCl was added to the solution and pH was adjusted to 8 by adding 2.5 μL of 50% w/v solution of Tris base prepared in $H_2^{18}O$. Then, DTT was added to be 1 mM and incubated at 37° C. for 1 hr followed by addition of IAC to be 2.5 mM and incubation for 1 hr in the dark. The resulting labeled peptide solution was diluted 50 μL with water and stored at −20° C. until further use.

Flow Injection and LC-MS/MS Analysis

Residual PFOA in different fractions were quantified by flow injection-MS analysis. Different concentrations of PFOA standard solution (25-400 pg) and the samples diluted 50000-times were dissolved in 0.1% formic acid-50% acetonitrile and injected into a flowing carrier stream consisting of 0.1% formic acid-50% acetonitrile at 40 µL/min using a Schimadzu LC 20 AD (Schimadzu Scientific Instruments, Columbia, Md., USA) that was directly connected to a quadrupole-time-of-flight mass spectrometer (QStar Elite, Applied Biosystems, Foster City, Calif., USA) equipped with an electro spray ion source. The (M-H)$^-$ ion (m/z 413) of PFOA was monitored in TOF-MS mode. A standard curve was plotted between various concentrations of PFOA and their corresponding chromatographic peak areas, and the PFOA concentration in each sample was determined using the standard curve.

Those skilled in the art will recognize, or be able to ascertain using no more than routine experimentation, numerous equivalents to the compounds and methods of use thereof described herein. Such equivalents are considered to be within the scope of this invention and are covered by the following claims. All of the above-cited references and publications are hereby incorporated by reference.

Having described the invention, we claim:

1. A method of extracting polypeptides from a biological sample, the method comprising:
    contacting the biological sample with an extraction reagent to form a solution of the polypeptides of the biological sample and the extraction reagent, the extraction reagent being at a concentration effective to solubilize the polypeptides in the biological sample, the extraction reagent comprising perfluorooctanoic acid; and
    separating the solution of the extraction reagent and the solubilized polypeptides from insoluble matter of the biological sample in the solution.

2. The method of claim 1, further comprising contacting the solution with a proteolytic enzyme to digest the polypeptides in the solution, wherein the proteolytic enzyme retains at least 80% of its enzymatic activity.

3. The method of claim 2, the concentration of perfluorooctanoic acid in the solution during proteolytic digestion being about 0.1% w/v to about 0.5% w/v.

4. The method of claim 1, the extraction reagent further comprising at least one of a reducing agent and an s-alkylating agent.

5. The method of claim 1, the extraction agent comprising up to 2% w/v perfluorooctanoic acid.

6. The method of claim 2, further comprising precipitating the polypeptides from the solution.

7. The method of claim 2, removing the perfluorooctanoic acid from the solution after separation of the insoluble matter of the biological sample in the solution.

8. The method of claim 7, the perfluorooctanoic acid being removed from the solution by evaporation.

9. The method of claim 7, the perfluorooctanoic acid being removed from the solution by at least one of chromatography or solid phase extraction.

10. The method of claim 9, the perfluorooctanoic acid being removed by at least one of strong cation exchange chromatography, hydrophilic interaction chromatography, fluorous solid phase extraction, or anion exchange chromatography.

11. A method of extracting polypeptides from a biological sample, the method comprising:
    contacting the biological sample with an extraction reagent to form a solution of the polypeptides of the biological sample and the extraction reagent, the extraction reagent being at a concentration effective to solubilize the polypeptides in the biological sample, the extraction reagent comprising up to about 2% w/v perfluorooctanoic acid;
    separating the solution of the extraction reagent and the solubilized polypeptides from insoluble matter of the biological sample in the solution; and
    removing the perfluorooctanoic acid from the solution after separation.

12. The method of claim 11, further comprising contacting the solution with a proteolytic enzyme to digest the polypeptides in the solution, wherein the proteolytic enzyme retains at least 80% of its enzymatic activity.

13. The method of claim 12, the concentration of perfluorooctanoic acid in the solution during proteolytic digestion being about 0.1% w/v to about 0.5% w/v.

14. The method of claim 11, the extraction agent further comprising at least one of a reducing agent and an s-alkylating agent.

15. The method of claim 11, further comprising precipitating the polypeptides from the solution prior to removing the perfluorooctanoic acid.

16. The method of claim 11, the perfluorooctanoic acid being removed from the solution by evaporation.

17. The method of claim 11, the perfluorooctanoic acid being removed from the solution by at least one of chromatography or solid phase extraction.

18. The method of claim 11, the perfluorooctanoic acid being removed by at least one of strong cation exchange chromatography, hydrophilic interaction chromatography, fluorous solid phase extraction, or anion exchange chromatography.

19. A method of extracting polypeptides from a biological sample, the method comprising:
    contacting the biological sample with an extraction reagent to form a solution of the polypeptides of the biological sample and the extraction reagent, the extraction reagent being at a concentration effective to solubilize the polypeptides in the biological sample, the extraction reagent comprising up to about 2% w/v perfluorooctanoic acid; contacting the solution with a proteolytic enzyme to digest the polypeptides in the solution, the concentration of perfluorooctanoic acid in the solution during proteolytic digestion being about 0.1% w/v to about 0.5% w/v;

separating the solution of the extraction reagent and the solubilized polypeptides from insoluble matter of the biological sample in the solution; and removing the perfluorooctanoic acid from the solution after separation.

20. The method of claim 19, the extraction reagent further comprising at least one of a reducing agent and an s-alkylating agent.

21. The method of claim 19, the perfluorooctanoic acid being removed from the solution by evaporation.

22. The method of claim 19, the perfluorooctanoic acid being removed by at least one of strong cation exchange chromatography, hydrophilic interaction chromatography, fluorous solid phase extraction, or anion exchange chromatography.

* * * * *

UNITED STATES PATENT AND TRADEMARK OFFICE
CERTIFICATE OF CORRECTION

PATENT NO. : 8,921,515 B2  
APPLICATION NO. : 13/727646  
DATED : December 30, 2014  
INVENTOR(S) : Masaru Miyagi et al.

Page 1 of 1

It is certified that error appears in the above-identified patent and that said Letters Patent is hereby corrected as shown below:

In the claims

Column 27, line 56, should read --9. The method of claim 7, the perfluoriooctanoic acid being--

Signed and Sealed this  
Third Day of November, 2015

Michelle K. Lee  
*Director of the United States Patent and Trademark Office*